United States Patent [19]

Isenberg et al.

[11] Patent Number: 5,359,895
[45] Date of Patent: Nov. 1, 1994

[54] PROCESS AND DEVICE FOR THE ULTRASONIC TESTING FOR WELDS BETWEEN PLASTICS PACKAGING AND COVER FOILS

[75] Inventors: Heinz H. Isenberg, Braunschweig; Göran Vogt, Burgwedel-Wettmar; P. Gerhard Althaus, Garbsen, all of Germany

[73] Assignees: Schmalbach-Lubeca AG, Braunschweig; MPV MEB-und Pruftechnik Vogt GmbH, Burgwedel, both of Germany; a part interest

[21] Appl. No.: 930,677
[22] PCT Filed: Mar. 19, 1991
[86] PCT No.: PCT/DE91/00232
  § 371 Date: Oct. 5, 1992
  § 102(e) Date: Oct. 5, 1992
[87] PCT Pub. No.: WO91/15759
  PCT Pub. Date: Oct. 17, 1991

[30] Foreign Application Priority Data

Apr. 15, 1990 [DE] Germany .................. 4010952

[51] Int. Cl.$^5$ .................................. G01M 3/00
[52] U.S. Cl. ........................... 73/582; 73/592; 73/52
[58] Field of Search ............ 73/582, 588, 592, 600, 73/49.3, 52, 45.4, 41.2, 45

[56] References Cited

U.S. PATENT DOCUMENTS

| | | |
|---|---|---|
| 3,384,733 | 5/1968 | Burbank et al. |
| 4,295,375 | 10/1981 | Ganglbauer .................. 73/582 |
| 4,697,452 | 10/1987 | Prakken ....................... 73/49.3 |
| 4,821,573 | 4/1989 | Nagata et al. ................. 73/52 |

FOREIGN PATENT DOCUMENTS 0039494  5/1981  European Pat. Off.

OTHER PUBLICATIONS

IBM Technical Disclosure Bulletin, vol. 32, (1), "Inspection of Adhesion in Magneto-Optic Thin Film Structure". Jun. 1989, Armonk, N.Y., US, pp. 258-259.

Primary Examiner—Tom Noland
Assistant Examiner—Helen C. Kwok
Attorney, Agent, or Firm—Eckert Seamans Cherin & Mellott

[57] ABSTRACT

A process and an apparatus for the ultrasonic testing of welds between plastic packaging like food trays and cover foils. The welded joint between the tray and cover foil is periodically exposed to pulses of ultrasonic radiation. The pulses pass through the weld and are picked up or received by a receiver. The amplitude of the received pulses is evaluated. The cross-section of the beam of ultrasonic radiation is so small that the radiation only passes through the weld itself. The packages and the ultrasonic tester are moved relative to each other in order to examine the whole circuit of the weld. The pulse rate is such that the weld areas covered by successive pulses overlap.

20 Claims, 3 Drawing Sheets

PROCESS AND DEVICE FOR THE ULTRASONIC TESTING FOR WELDS BETWEEN PLASTICS PACKAGING AND COVER FOILS

BACKGROUND OF THE INVENTION

1. Field of the Invention

The invention pertains to a process for the ultrasonic testing of heat-sealed joints between plastic packages (especially trays for ready-to-eat meals) and cover films. The invention also pertains to equipment for performing this process.

2. Description of the Related Art

Dishlike plastic packages in various shapes for packaging foods are well known. After they have been filled, they are sealed with a cover film, which is not removed until immediately before the food is to be eaten. The stability of foods packaged in this way depends, among other factors, on the tightness of the heat-sealed joint between the cover film and the dishlike package. When the film is applied to the edge of the package, it frequently happens that wrinkles develop, plastic particles become heat-sealed in the joint bulges form, or food particles are trapped between the cover film and the package. If no bond forms between the plastic package and the cover film in such places, the package is not sealed, and then oxygen and contaminants can reach the food through these defects. Furthermore, the food may be able to run out etc. Therefore, to improve the probability that the packaged food will remain safe in accordance with applicable food laws until the expiration date that is printed on the package, it is necessary to make sure that the heat-sealed joint is completely closed all around the package, i.e., that there are no defects in the heat-sealed joint.

Accordingly, the goal of the invention was to develop a process and equipment for testing heat-sealed joints of the type described above. A further goal of the invention was to be able to perform this process with both a high degree of accuracy and reproducibility and with as much speed as possible.

SUMMARY OF THE INVENTION

Surprisingly, it was found that by focusing a beam of ultrasonic radiation of relatively small cross section exclusively on the heat-sealed joint, very reliable information can be obtained about the quality of the joint. Since the ultrasonic radiation passes exclusively through the heat-sealed joint, boundary effects of the regions on either side of the heat-sealed joint, where air bubbles, pieces of food or other undesirable elements may be present between the cover film and package, do not enter into the measuring result. Due to the overlapping of the areas along the heat-sealed joint through which the ultrasonic radiation passes, continuous testing is achieved. The overlapping can be relatively broad, e.g., more than 50%, so that one and the same point of a heat-sealed joint is tested several times. Perpendicular transmission of the ultrasonic radiation, which is ensured by suitable measures in the course of the process and in the operation of the equipment, makes it possible to clearly distinguish signals caused by defects in the joint from signals caused by normal fluctuations in the area of the test system, e.g., in the thickness of the edge of the tray etc. In this connection, it should be noted that defects produce abrupt changes in the ultrasonic signal, even though the changes may be quite small, whereas geometric deviations cause no spontaneous change in the signal amplitude. Fluctuations in the amplitude of the transmitted ultrasonic pulse can be averaged out by sufficiently broad overlapping of the areas covered by the pulse. Finally, the plastic package and ultrasonic test device must move relative to each other in such a way that the entire heat-sealed joint, which forms a closed curve, is scanned once with complete certainty.

The process of the invention and the equipment used to perform it allow relatively fast testing of a heat-sealed joint. For example, the testing of a heat-sealed joint between the tray and cover film of a ready-to-eat meal can be performed in less than a second. This has the advantage that the equipment of the invention can be integrated in an existing packaging plant without having to reduce the plant's cycle time. In a further modification with respect to the process, it is proposed that the ultrasonic testing be performed with its own cycle control running independently of the cycle time of the packaging plant itself. This eliminates the need for connections or coordination with the packaging plant itself, and the testing can be started and stopped relatively quickly. In accordance with the process, the heat-sealed packages are conveyed by a conveyor belt to a baffle plate, which diverts the packages one by one into the ultrasonic testing unit, in which the heat-sealed joints are tested. The entire passage takes only a few seconds, e.g., three seconds. The packages are then lifted back onto the conveyor belt. Untight packages are sorted out after they have been placed back on the convevor belt, while packages with intact heat-sealed joints remain on the conveyor belt. The acoustic coupling of the transmitting and receiving ultrasonic probes is effected through a water advance interval. Either both probes are located in a water bath, into which the heat-sealed joint or at least the portion of the heat-sealed joint currently being tested is also immersed, or the coupling is effected by water jets, i.e., for example, probes of the type described in U.S. Pat. Nos. 3,255,626, 3,485,088, 3,908,455 and 4,403,510 or in European Patent 119 096. In both cases (immersion method or coupling by water jets), it has been found to be advantageous to work in a tank to catch or hold the water.

In regard to the equipment, a so-called "bypass system" has proven to be very effective. It can be connected to existing packaging plants. The only thing needed is a short stretch of conveyor belt, up to which the system can be pushed.

With respect to the equipment, the testing of circular plastic packages is especially simple and advantageous because in this case only the traylike package must be turned about its own axis, while the ultrasonic test line can remain stationary. However, the process of the invention also allows the testing of noncircular packages. In this case, the package to be tested is placed in a matching mount; this mount ensures geometric coordination. The mount with the package is turned about a quasi-center. In addition, the ultrasonic test line is moved transversely to the transport direction 44, so that deviations from the circular shape can be eliminated. Finally, rectangular packages can also be tested by covering heat-sealed joint areas running at right angles to the linear direction of transport by probes which are carried along in the direction of transport but which are simultaneously moved in the transverse direction.

Transmission of the ultrasonic radiation through the heat-sealed joint was wound to be crucially important;

testing on the basis of reflected sound signals does not yield satisfactory results.

The ultrasonic testing of packaged foods is basically already known from EP-A-269 185. In that process, ultrasonic radiation is transmitted through the food itself for the purpose of detecting gas bubbles caused by fermentation before the fermentation has progressed so far that the package shows noticeable bulging. There is no preventive test that can be performed immediately after the food has been packaged, but rather deterioration of the packaged food due to fermentation must already have occurred for the previous ultrasonic test to be able to sort it out. Testing of the heat-sealed joint is not performed.

Overlapping of the joint areas covered by the individual ultrasonic pulses is understood to mean the overlapping of a first ultrasonic pulse by the following ultrasonic pulse by at least 2% and preferably at least 20% of the ultrasonically covered area of the heat-sealed joint. The overlapping is usually less than 100%. 100% overlapping occurs when exactly the same area covered by a first pulse is covered again by a second pulse.

Noncircular, e.g., oval, ultrasonic coverage areas, in which the cross-sectional length is greater than the cross-sectional width, have been found to be very advantageous. In this case, the greater length dimension of the ultrasonic coverage area should lie essentially parallel to the course of the heat-sealed joint line.

BRIEF DESCRIPTION OF THE DRAWING FIGURES

Additional features and advantages of the invention are described in the other claims and in the following description of a specific embodiment of the invention, which is explained in detail with reference to the drawings. It is understood that the invention is in no way limited by this example.

DESCRIPTION OF THE PREFERRED EMBODIMENTS

Successively filled plastic packages 22 that have been sealed with cover films are located on a conveyor belt 20 moving perpendicularly to the plane of the drawing, i.e., into the plane of the drawing. These untested packages are conveyed towards an obliquely positioned baffle plate 24, which diverts them from their path and, as is shown for package 23, causes them to slide into the ultrasonic testing device, which will be described below. If the ultrasonic testing is not to be performed, the baffle plate 24 is swung completely out of the path of the packages 22.

Figure 3:
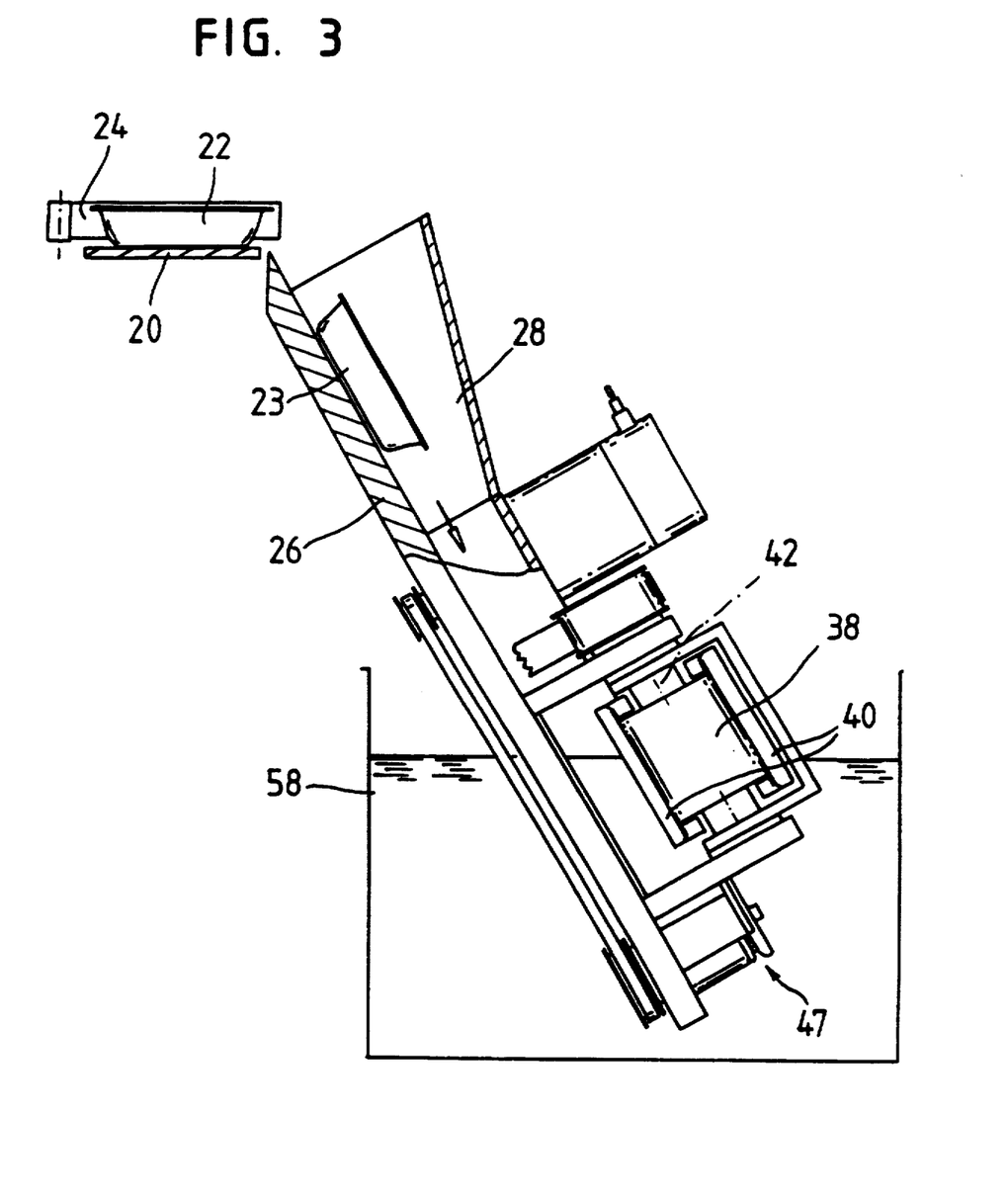
FIG. 3 shows a front view of the test device with the conveyor belt and a water tank.

As FIG. 3 shows, the ultrasonic testing device forms a feed hopper, which is bounded by a plate 26 and a U-shaped sheet-metal guide 28. As will be described below, the plate 26 holds all parts of the device. It is inclined at an angle of 30° from the vertical. The packages 22 slide on their bottoms on the plate 26, so that the cover film remains a certain distance from the surface of the plate 26 and is thus protected. The heat-sealed joint, whose tightness is to be tested, is located at 32.

Figure 1:
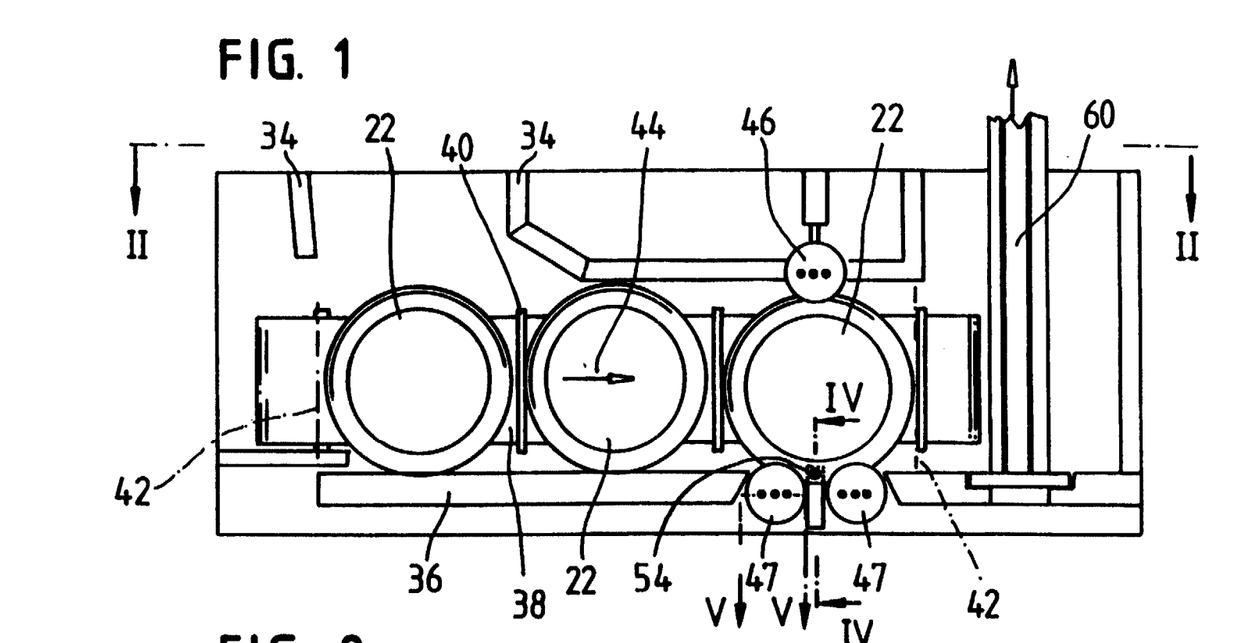
FIG. 1 shows a lateral cross section of a test device along line I—I in FIG. 2.
Figure 2:
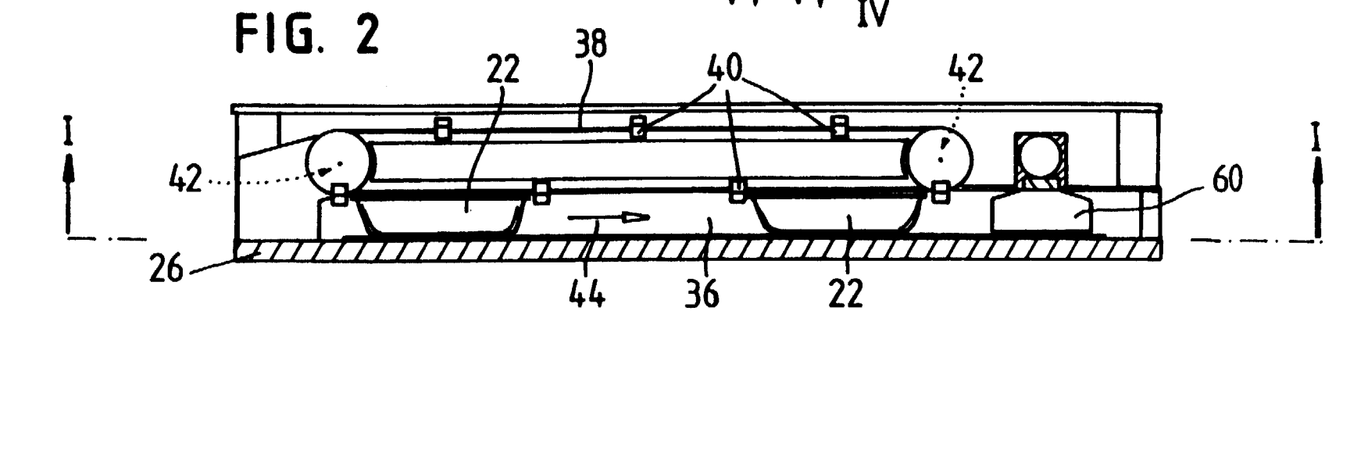
FIG. 2 shows a cross section along line II—II in FIG. 1.

The package 22 to be tested is guided between guide jaws 34 by parts of the sheet-metal guide 28 that are positioned transverse to the direction of conveyance of the conveyor belt 20 and falls into the area between a conveyor belt 38 and the plate 26. The conveyor belt 38 has catches 40 arranged at distances that are adjusted to the package 22. The system is designed in such a way that the package can only slide between two catches 40 in the space between the conveyor belt 38 and the plate 26. The catches 40 extend so far towards the plate 26 that a package that is sliding down first strikes them and then slides further only when a sufficiently large gap becomes available for it between two catches 40. This situation is shown in FIGS. 1 and 2. The package 22 is supported towards the bottom by a support ledge 36. It is arranged in such a way that the center of the packages 22, which are circular in the specific example shown here, lies on the center line of the conveyor belt 38.

In a modification of the process, the conveyor belt 38 can also be stopped in the position shown in FIGS. 1 and 2 until a package 22 is located in the position shown at the far left.

The conveyor belt 38 runs around in a closed loop. It is guided over two rollers 46, 47, at least one of which is driven. The rollers rotate about axes 42 that run parallel to the surface of the plate 26. As FIGS. 1 and 2 show, the distance between the respective axes 42 of the two rollers 46 and 47 is slightly greater than three times the diameter of the packages 22.

The conveyor belt 38 conveys the packages to the right in FIGS. 1 and 2 in the direction of arrow 44. The packages arrive at an intermediate position, which is shown in FIG. 1 as the middle position of the packages 22, and then finally reach the actual test position, which is shown on the right in FIGS. 1 and 2. Thus the conveyor belt 20, the baffle plate 24, the feed hopper and the conveyor belt 38 cooperatively supply unrested packages successively to the test position. They are held at the top by suitably extended, now horizontally running guide jaws 34 and are supported at the bottom on the support ledge 36.

Figure 5:
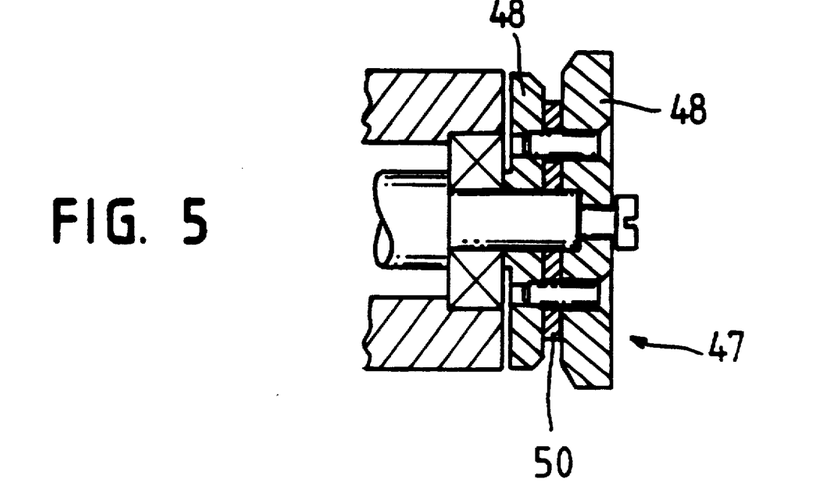
FIG. 5 shows a cross section along line V—V in FIG. 1.

The ultrasonic test position has respective axes 42 of the two rollers 46 and 47 three driven, grooved rollers 46, 47, one of which is shown in cross section in FIG. 5. As FIG. 1 shows, two lower rollers 47 are located in a continuation of the support ledge 36 at a distance from each other that is selected so narrow that the ultrasonic test device, which will be discussed later, has just enough room between them. They are mounted at the same height.

A single roller 46 is arranged centrally above the two lower rollers 47. The centers of the rollers 46, 47 form the vertices of an isosceles triangle, whose apex angle (at roller 46) is selected as acute as possible.

The purpose of the rollers 46, 47 is to tune the packages 22 about their centers and at the same time to guide them exactly. During the turning movement of the package 22, the conveyance of the packages 22 by the conveyor belt 38 is momentarily stopped.

As FIG. 1 shows, in the test position, the packages 22 are positioned somewhat lower than before, i.e., as long as they are supported by the support ledge 36. To allow them to enter the space between the three rollers 46, 47, the upper roller 46 is briefly raised, for which purpose a cylinder (shown schematically) is provided above this roller. As a package 22 arrives at the test position, it drops down slightly onto rollers 47 and triggers a control pulse, which in response thereto the roller 46 drops back down and the ultrasonic test is performed with timing that is determined by the ultrasonic test device itself. After the roller 46 drops back down, the turning movement is performed.

The three structurally identical rollers 46, 47 consist essentially of three disks, namely, two outer, beveled guide disks 48 and a middle, driver disk 50, which is knurled on the outside. The outer edge of the latter disk grips the edge of the tray by friction. The driver disk 50 is selected with such a thickness that the edge of the tray with the cover film on it is maintained between the two guide disks 48 with as little play as possible.

Figure 4:
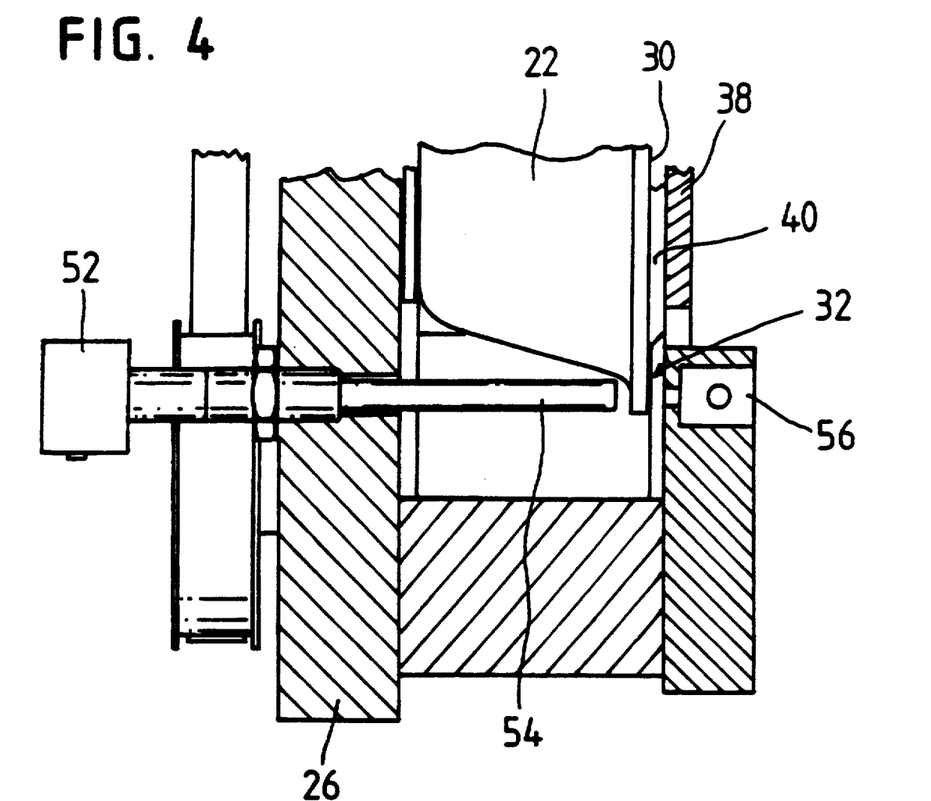
FIG. 4 shows a cross section along line IV—IV in FIG. 1.

The ultrasonic test will now be described especially with reference to FIG. 4. An ultrasonic transmitter 52 is mounted in a drill hole in plate 26. It transmits short-duration ultrasonic pulses with a frequency of, for example, 10 MHz at a high pulse rate of, for example 1 to 5 kHz. A sound guide tube 54 with an inside diameter of 3 mm is mounted on the transmitter and extends to the immediate vicinity of the edge of the tray. It has an oval shape at its free outlet end, such that the major axis of the oval coincides with the direction of the heat-sealed joint to be tested. In this way, the ultrasonic transmission area on the heat-sealed joint is shaped such that the pulses have a cross-section which includes a dimension of about 2 to 2.5 mm in the direction transverse to the longitudinal course of the heat-sealed joint. The circular package disclosed have heat-sealed joints extended along and defining courses. The shape of the outlet end of the sound guide tube 54 and the exact geometric coordination between the sound guide tube 54 and the edge of the package 22 with the heat-sealed joint ensure that only the actual area of the heat-sealed joint is exposed to the ultrasonic radiation. In this connection, the geometric coordination is guaranteed essentially by the two rollers 47, which are positioned in the immediate vicinity of the ultrasonic test.

The ultrasonic pulses which have passed through the edge of the package 22 and the cover film in the area of the heat-sealed joint are picked up or received by an ultrasonic receiver 56. The circumferential speed with which the package 22 is turned and the repeating frequency with which the ultrasonic pulses are transmitted by the transmitter 52 are mutually adjusted in such a way that the oval ultrasonic exposure areas on the heat-sealed joint overlap each other.

Apparatus for the generation and evaluation of the ultrasonic pulses are already well known, i.e. state-of-the-art methods can be used. In the practical performance of tests with one type of packages 22, it was found that the ultrasonic signals fluctuate by 2 dB due to deviations from perpendicular transmission through the edge of the package 22 and other factors. Changes greater than 4 to 6 dB can be given as defects in the heat-sealed joint. Another decision criterion that can be used is based on the fact that defects lead to abrupt changes in the ultrasonic signal, while other geometric changes produce slower changes in the ultrasonic signal.

In the specific embodiment of the invention shown here, acoustic contact or coupling between the probe and the test specimen is made through water. For this reason, as FIG. 3 shows, the test device is located in a water tank 58, which is filled to a sufficiently high level that at least the lower, currently tested regions of the edges of the trays are submerged in the water.

During the test, the package 22 is turned at least once about its own axis. If enough time is available, the package can be rotated a second time. After the ultrasonic test has been performed, the conveyor belt 38 moves forward, and the package 22 advances to the area of a lifting device 60, which lifts the package in the direction opposite the direction in which it previously slid downward. The package 22 is thus lifted back to the plane of the conveyor belt 20 until it tips back onto this conveyor belt. The package then reassumes the position shown in FIG. 3 as the initial position. A baffle plate is then used to sort out those tested packages that were evaluated as defective during the ultrasonic test. In another modification, the lifting device can also be used to sort good and bad packages.

The equipment of the invention can be coordinated with an existing packaging line in a bypass operation. Attachment and detachment can be accomplished by a few manual operations. Once the test equipment is connected to the packaging line, a decision can be made for each individual package on the conveyor belt 20 whether that package should be tested or not. This is accomplished by control of the baffle plate 24.

To simplify maintenance of the system, the conveyor belt 38 is arranged so that it can be swung out around one of its axes 42. If one wishes not to use water (or another suitable liquid) as the acoustic coupling medium and would rather perform dry measurements, it is also possible to maintain the test probes 52, 56 in rubbing contact with the edge of the package 22 or cover film 30. Mixed forms, i.e., acoustic coupling of the transmitter 52 through water but acoustic coupling of the receiver by rubbing contact, or the like, are also possible.

Higher test frequencies, e.g., 15 MHz and higher, have been found to be more suitable for this test than lower frequencies, e.g., 3 MHz. The invention also allows the testing of yogurt containers, drug packages etc.

In a modified embodiment of the invention, in which the equipment is otherwise identical, the probes 52, 56 are replaced by probes of types that are already known, for example, from the four US patents and the European patent cited above. The water jets are directed at the heat-sealed joint 32 from both sides in such a way that the degree of overlapping is as complete as possible, i.e., the ultrasonic pulse can pass through linearly. The probes 52, 56 are connected by well-known means to a water reservoir, from which they are continuously supplied with water by a pump. A sound guide tube is unnecessary under these circumstances. Aside from these modifications, the same equipment can be used as described above.

However, as far as the process is concerned, when acoustic coupling by water jets is used, in contrast to the immersion method described above, the water in the tank 58 is maintained at such a depth that the water jets issuing from the probes 52, 56 are above the level of the water.

The ultrasonic transmission areas are generally circular, but the use of oblong transmission areas is advantageous; in this case, the larger dimension of the transmission area is aligned with the longitudinal direction of the heat-sealed joint.

We claim:

1. Process for the ultrasonic testing of a heat-sealed joint between a plastic package in a form of a tray for ready-to-eat meals and a cover film, in which:

packages are supplied successively to a test position of an ultrasonic test device:

a transmitter of ultrasonic radiation is acoustically coupled to the heat-sealed joint of a package at the test position through a water advance interval in a form of a water jet, the heatsealed joint is periodically exposed to pulses of ultrasonic radiation in an ultrasonic transmission area, the pulses passing through the heat-sealed joint are received, and an amplitude of the pulses is evaluated, the ultrasonic transmission area is sufficiently small that the pulses pass only through a region of the heat-sealed joint itself, the package at the test position and the transmitter are moved relative to each other in order to pass the ultrasonic transmission area at least once along a whole course of the joint, the pulses are supplied at a pulse rate selected such that one area on the heat-sealed joint covered by one pulse overlaps another area on the heat-sealed joint covered by a successive pulse, and a baffle plate is provided for the packages being conveyed on a conveyor belt, which baffle plate deflects packages that are evaluated as defective.

2. Process in accordance with claim 1, wherein the package at the test position is evaluated as defective if an abrupt change in the reception of the pulses is detected.

3. Process in accordance with claim 1, wherein the packages are circular trays defining turning axes, which are turned about said turning axes.

4. Process in accordance with claim 1, wherein a start of a test is initiated by a control pulse, which is received when a package to be tested has arrived at the test position, and that the test is then performed with timing that is determined by the ultrasonic test device itself.

5. Process in accordance with claim 1, wherein untested packages moving on a conveyor belt are diverted from conveyance on the conveyor belt by a diverter and fall into a feed hopper, and that tested packages are lifted by a lifting device in such that the tested packages tip back onto the conveyor belt.

6. Process in accordance with claim 1, wherein the transmitter is moved while the package at the test position remains stationary.

7. Process in accordance with claim 1, wherein the ultrasonic transmission area is noncircular and has a smaller height than width, such that the width defines an axis aligning with the course of the heat-sealed joint.

8. Equipment for the ultrasonic testing of a heat-sealed joint between a plastic package in a form of a tray for ready-to-eat meals and a cover film, comprising:

means for supplying untested packages successively to a test position;

an ultrasonic test device associated with the test position, which includes:
  (i) a transmitter for periodically transmitting pulses of ultrasonic radiation at a selectable pulse rate to the heat-sealed joint,
  (ii) means for acoustically coupling the transmitter with the heat-sealed joint of the package at the test position so that the pulses pass only through a region of the heat-sealed joint itself,
  (iii) a receiver for receiving the pulses passing through the heatsealed joint, and
  (iv) means for evaluating an amplitude of the received pulses: means for imparting relative movement between the package at the test position and the transmitter in order to pass the ultrasonic transmission area at least once along a whole course of the heat-sealed joint of the package at the test position;

means or adjusting the pulse rate such that one area on the heat-sealed joint covered by one pulse overlaps another area on the heat-sealed joint covered by a successive pulse; and, a conveyor belt associated with the ultrasonic test device and a baffle plate associated with the conveyor belt, wherein tested packages are conveyed on the conveyor belt and the baffle plate deflects the tested packages that are evaluated as defective; and, wherein, each package is a circular tray defining a turning axis; and said means for imparting relative movement includes three rollers arranged for guiding and moving an edge of the package at the test position such that said package turns about said turning axis, the rollers having centers cooperatively defining vertices of an acute isosceles triangle such that two rollers closely neighbor one another, and the transmitter and receiver being located between said two closely neighboring rollers.

9. Equipment in accordance with claim 8, wherein the ultrasonic test device further includes a plate, which is arranged obliquely at an angle of about 30°.

10. Equipment in accordance with claim 8 wherein the conveyor belt has catches.

11. Equipment in accordance with claim 9, wherein the conveyor belt has catches.

12. Apparatus for the ultrasonic testing of a heat-sealed joint between a cover film and a plastic package in a form of a tray for ready-to-eat meals, the heatsealed joint of each package extending along and defining a course; said apparatus comprising:

means for supplying untested packages successively to a test position;

an ultrasonic test device associated with the test position, which includes:
  (i) a transmitter for periodically transmitting pulses of ultrasonic radiation at a selectable pulse rate to the heat-sealed joint of the package at the test position,
  (ii) means for acoustically coupling the transmitter with the heat-sealed joint of the package at the test position so that the pulses pass only through a region of the heat-sealed joint itself,
  (iii) a receiver for receiving the pulses passing through the heat sealed joint, and
  (iv) means for evaluating an amplitude of the received pulses; means for imparting relative movement between the package at the test position and the transmitter in order to pass the ultrasonic transmission area at least once along the whole course of the heat-sealed joint;

means for adjusting the pulse rate such that one area on the heat-sealed joint covered by one pulse overlaps another area on the heat-sealed joint covered by a successive pulse; and, a conveyor belt associated with the ultrasonic test device and a baffle plate associated with the conveyor belt, wherein tested packages are conveyed on the conveyor belt and the baffle plate deflects the tested packages that are evaluated as defective during the ultrasonic test.

13. Apparatus in accordance with claim 12, wherein said means for evaluating the received pulses is responsive to change between successive pulses such that the package at the test position is evaluated as defective if an abrupt change in the reception of the pulses is detected.

14. Apparatus in accordance with claim 12, wherein the ultrasonic test device further includes means for responding to the arrival at the test position of one of the packages, which in response starts the performance of an ultrasonic test with timing that is determined by the ultrasonic test device itself.

15. Apparatus in accordance with claim 12, wherein the means for supplying untested packages includes the conveyor belt, a feed hopper associating the conveyor belt with the ultrasonic test device, and means for diverting untested packages from conveyance on the conveyor belt to fall into the feed hopper; and, further comprises:
   a lifting device, which associates the ultrasonic test device with the conveyor belt, for lifting tested packages up from the ultrasonic test device such that the tested packages tip back onto the conveyor belt.

16. Apparatus in accordance with claim 12, wherein the means for imparting relative movement moves the transmitter while the package at the test position remains stationary.

17. Apparatus in accordance with claim 12, wherein the ultrasonic transmission area is noncircular and has a smaller height than width, such that the width defines an axis; the course of the heat-sealed joint of the package at the test position defining a middle line; wherein the axis of the width of the transmission area generally aligns with the middle line course of the heat-sealed joint of the package at the test position.

18. Apparatus in accordance with claim 15, wherein the feed hopper includes a plate, which is arranged obliquely at an angle of about 30°.

19. Apparatus in accordance with claim 12, wherein said means for imparting relative movement imparts movement to the package at the test position.

20. Equipment in accordance with claim 8, wherein said means for supplying untested packages includes the conveyor belt, a feed hopper associating the conveyor belt with the ultrasonic test device, and means for diverting untested packages from conveyance on the conveyor belt to fall into the feed hopper; and, further comprises:
   a lifting device, which associates the ultrasonic test device with the conveyor belt, for lifting tested packages up from the ultrasonic test device such that the tested packages tip back onto the conveyor belt.

* * * * *

UNITED STATES PATENT AND TRADEMARK OFFICE
CERTIFICATE OF CORRECTION

PATENT NO. : 5,359,895
DATED : November 1, 1994
INVENTOR(S) : Isenberg et al.

It is certified that error appears in the above-indentified patent and that said Letters Patent is hereby corrected as shown below:

Column 1, line 23, insert --,-- after "joint".

Column 2, line 68, change "wound" to --found--.

Column 4, line 39, change "unrested" to --untested--.

Column 4, lines 44-45, delete "respective axes 42 of the two rollers 46 and 47" and replace with --means for imparting relative movement between the package at the test position and the ultrasonic signal. One way to accomplish relative movement is by--.

Column 4, line 57, change "tune" to --turn--.

UNITED STATES PATENT AND TRADEMARK OFFICE
CERTIFICATE OF CORRECTION

PATENT NO. : 5,359,895
DATED : November 1, 1994
INVENTOR(S) : Isenberg, et al

It is certified that error appears in the above-indentified patent and that said Letters Patent is hereby corrected as shown below:

Column 8, line 5, change "or" --for--.

Signed and Sealed this

Fourteenth Day of March, 1995

Attest:

BRUCE LEHMAN

*Attesting Officer*     *Commissioner of Patents and Trademarks*